United States Patent [19]

Murofushi et al.

[11] 4,376,219

[45] Mar. 8, 1983

[54] PROCESS FOR PREPARING AN ETHER HAVING TERTIARY ALKYL GROUP

[75] Inventors: Toshiaki Murofushi, Fuji; Atsushi Aoshima, Yokohama, both of Japan

[73] Assignee: Asahi Kasei Kogyo Kabushiki Kaisha, Osaka, Japan

[21] Appl. No.: 340,668

[22] Filed: Jan. 19, 1982

[30] Foreign Application Priority Data

Jan. 22, 1981 [JP] Japan .................................... 56-8414

[51] Int. Cl.$^3$ ............................................. C07C 41/06
[52] U.S. Cl. ..................................... 568/697; 568/672; 568/678
[58] Field of Search ........................ 568/697, 672, 678

[56] References Cited

U.S. PATENT DOCUMENTS 3,135,807 6/1964 Grosselli et al. ................... 568/697
4,175,210 11/1979 Selwitz et al. ..................... 568/697
4,262,145 4/1981 Selwitz et al. ..................... 568/697

FOREIGN PATENT DOCUMENTS 54-14909 2/1979 Japan ................................. 568/697

Primary Examiner—Howard T. Mars

Attorney, Agent, or Firm—Sprung, Horn, Kramer & Woods

[57] ABSTRACT

In a process for preparing an ether having a tertiary alkyl group by the reaction of a primary or secondary alcohol with the tertiary olefin in a tertiary olefin-containing mixed hydrocarbon, said reaction is carried out in the presence of an adduct of the starting alcohol with a heteropoly acid or salt thereof containing at least one member selected from the group consisting of P, Si, B, Ge, As, Se, Ti, Zr, Mn, F, U, Ce and Th as a central element, at least Mo and/or W as a coordinating element and at least one member selected from the group consisting of H, Li, Na, K, Rb, Cs, $NR^4R^5R^6R^7$ wherein $R^4$, $R^5$, $R^6$ and $R^7$ are hydrogen atoms or alkyl groups, Mg, Ca, Ba, Zr, Cr, Mn, Fe, Co, Mi, Cu, Ag, Zn, Cd, Hg, Al, Pb and Bi as cations, the ratio of the number of the coordinating elements to the number of the central elements being 2.5 to 12, said adduct being substantially in the solid phase, under a pressure higher than the pressure at which said mixed hydrocarbon containing the tertiary olefin is kept in the liquid phase. The reaction under the above conditions enables the extreme reduction of the degree of excess of the alcohol and the enhancement of the conversion of said tertiary olefin.

9 Claims, 1 Drawing Figure

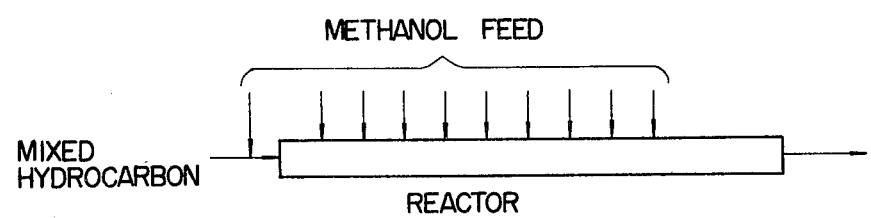

PROCESS FOR PREPARING AN ETHER HAVING TERTIARY ALKYL GROUP

This invention relates to a process for preparing an ether having a tertiary alkyl group from the tertiary olefin in a tertiary olefin-containing mixed hydrocarbon and a primary or secondary alcohol.

Ethers having tertiary alkyl groups, for example, tert-butyl methyl ether and tert-amyl methyl ether, have been used as an octane number improver of gasoline.

The isobutylene in a C4 olefin mixture is selectively reacted with an alcohol to remove the isobutylene from the mixture and highly pure 1-butene is obtained by distilling the mixture. This is one of the objects of this invention.

As the process for preparing ethers having a tertiary alkyl group from tertiary olefins and alcohols, there have hitherto been known the sulfuric acid process, the ion-exchange resin process, the vapor-phase process employing heteropoly acids or salts thereof and the homogeneous liquid-phase process employing the heteropoly acids. The sulfuric acid process has problems of the corrosion and the recovery of the catalyst, and the ion-exchange resin process has disadvantages that an excess of an alcohol is required for improving the conversion of tertiary olefins and said excessive alcohol forms an azeotropic mixture with the hydrocarbons and/or the resultant ethers, wherefore the purification step thereof becomes complicated. In the vapor-phase process employing heteropoly acids or salts thereof, the polymerization of the tertiary olefins tends to be caused. The homogeneous liquid-phase process employing heteropoly acids or salts thereof has problems of the formation of an azeotropic mixture of the hydrocarbons and/or the resultant ethers with the alcohols due to the effluence of the unreacted alcohol and catalyst from the reaction system, resulting in complication of the purification step and decomposition of the resulting ether.

As a result of extensive research on a process for producing an ether having a tertiary alkyl group by reacting a primary or secondary alcohol with the tertiary olefin in a tertiary olefin-containing mixed hydrocarbon by which the excess amount of the primary or secondary alcohol is kept small, and the conversion of the tertiary olefin is improved, whereby the purification step is prevented from complication due to the azeotropy of the hydrocarbons and/or the resultant ether with the alcohol, and the amount of the resultant ether recycled to the reaction system by the azeotropy of the alcohol with the ether can be made extremely small, and by which process the ether produced is prevented from decomposition in the distillation step due to the effluence of the catalyst, the present inventors have found that said object can be achieved by carrying out the reaction under a pressure higher than the pressure at which the mixed hydrocarbon containing the tertiary olefin is kept in the liquid phase in the presence of an adduct of the starting alcohol with a heteropoly acid or a salt thereof, the said adduct being in the solid phase.

In the conventional processes, in order to allow 98% or more of the tertiary olefin to react with the alcohol, the amount of the unreacted alcohol becomes 20 mole% or more based on the resultant ether, and the formation of an azeotropic mixture of the unreacted alcohol with the resultant ether causes a large amount of the resultant ether to be recycled together with the unreacted alcohol. Furthermore, complicated operations such as distillation under pressure and the like are required for reducing the amount of the ether recycled. According to the process of this invention, however, the conversion of the tertiary olefin reaches 98% or more and the proportion of the effluent alcohol to the resultant ether can be made 2.0 mole% or less even when the molar ratio of the starting alcohol to the tertiary olefin is 1.0.

In preparing an ether having a tertiary alkyl group by reacting a tertiary olefin with an alcohol, the conventional hydrated heteropoly acid or a salt thereof has a low etherification activity and forms a tertiary alcohol, and a free heteropoly acid or a salt thereof which is not in the form of an adduct with water, an alcohol or the like tends to cause polymerization of the tertiary olefin. It has, however, now been found that when the reaction is conducted under such conditions as to keep the adduct of the starting alcohol with a heteropoly acid or salt thereof in the solid phase, a sufficient activity can be kept even at a low alcohol concentration in the reaction mixture and the reaction can be allowed to proceed without using an excess of the alcohol, and the amount of the alcohol in the reaction product can be made very small. Furthermore, it has been found that when the proportion of the alcohol to the tertiary olefin is low, the adduct of a heteropoly acid or a salt thereof with the alcohol is not dissolved in the reaction mixture, the deterioration of the catalyst can be prevented, and the decomposition of the ether is not caused during the distillation. (For example, in the case of a catalyst consisting of 10 g of phosphomolybdic acid supported on 40 g of silica, only less than 1 ppm of phosphomolybdic acid is dissolved in a mixture of 100 g of the mixed hydrocarbon and not more than 8 g of the starting alcohol.)

The tertiary olefin used in this invention may be an olefin represented by the formula,

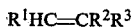

$$R^1HC\!\!=\!\!CR^2R^3$$

wherein $R^1$ is hydrogen or an alkyl group; $R^2$ and $R^3$ are alkyl groups, and include, for example, isobutylene, 2-methyl-1-butene, 2-methyl-2-butene, 2-methyl-1-pentene, 2-methyl-2-pentene, 2-ethyl-1-butene, 3-methyl-2-pentene, 2-methyl-1-hexene, and the like.

The tertiary olefin-containing mixed hydrocarbon used in the present invention is a mixture of the above-mentioned tertiary olefin with other hydrocarbons. As said other hydrocarbons, there may be used saturated hydrocarbons such as propane, butane, pentane and the like and olefins such as propylene, n-butene, n-pentene and the like. Examples of the tertiary olefin-containing mixed hydrocarbon include the so-called spent BB obtained by removing butadiene from the C4 fraction in the naphtha cracking process, the spent spent BB obtained by removing a part of the isobutylene from the spent BB, the C4 fraction obtained as a by-product in a fluid catalytic reactor for petroleum, the fraction obtained by catalytic dehydrogenation of n-butane, the C5 fraction in the naptha cracking process and the like. The concentration of the tertiary olefin in the tertiary olefin-containing mixed hydrocarbon is usually 50% by weight or less and may also be 5% by weight or less.

The primary or secondary alcohol used in the present invention may be a monohydric alcohol such as methanol, ethanol, n-propanol, isopropanol, n-butaol, isobutanol, sec-butanol, n-pentanol, n-hexanol or the like, or a polyhydric alcohol such as ethylene glycol, propylene glycol, 1,4-butanediol, or the like.

The process of this invention is particularly effectively to prepare selectively tert-butyl methyl ether from methanol and isobutylene in a mixed hydrocarbon having 4 carbon atoms.

The alcohol in the adduct of an alcohol with the heteropoly acid or salt thereof used in the present invention exists, even after the reaction, as the adduct with the heteropoly acid or salt thereof even after the reaction. Therefore, the amount of the starting alcohol fed in the present invention does not include the amount of the alcohol present as the adduct with the heteropoly acid or salt thereof before the reaction. The amount of the alcohol fed is usually 1.2 moles or less per mole of the tertiary olefin. Where the unreacted alcohol is in a small quantity and the tertiary olefin is intended to be sufficiently reacted, the alcohol is preferably used in an amount of 0.9 to 1.1 moles per mole of the tertiary olefin. The presence of an excess of the alcohol facilitates the dissolution of the adduct of an alcohol with the heteropoly acid or salt thereof. Therefore, it is not necessary to use the alcohol in an unnecessarily large amount.

The heteropoly acid or salt thereof used in the present invention contains at least one element selected from P, Si, B, Ge, As, Se, Ti, Zr, Mn, F, U, Ce and Th, preferably at least one element selected from P, Si, B and Ge, as the central element, and at least Mo and/or W as a coordinating element. A part of the coordinating element may be replaced by at least one element selected from V, Mn, Co, Ni, Cu, Zn and Fe, preferably V. The cation in the heteropoly acid or salt thereof is at least one of the cations of H, Li, Na, K, Rb, Cs, $NR^4R^5R^6R^7$ in which $R^4$, $R^5$, $R^6$ and $R^7$ are hydrogen atoms or alkyl groups, Mg, Ca, Ba, Zr, Cr, Mn, Fe, Co, Ni, Cu, Ag, Zn, Cd, Hg, Al, Pb and Bi, and preferred are the cations of H, Na, Zn, Al and Pb. $H^+$ is most preferable.

The ratio of the number of the coordinating elements to the number of the central elements to be used is usually from 2.5 to 12, preferably from 9 to 12. The heteropoly acid or salt thereof used in the present invention may be a mixture of at least two heteropoly acids or a mixture of at least two heteropoly acid salts. The heteropoly acid or salt thereof in the present invention must be an adduct with the starting alcohol. The hydrate of the above heteropoly acid or salt thereof must be dehydrated by treatment under vacuum or calcination at high temperature and then converted into an adduct with the starting alcohol, or the water of the hydration is replaced with a large amount of the starting alcohol to form an adduct with the alcohol, or the water of hydration is reacted with an olefin or the like to remove the water and then the dehydrated heteropoly acid or salt thereof is converted to an adduct with the starting alcohol.

The adduct of the starting alcohol with heteropoly acid or salt thereof in this invention may be solid-phase heteropoly acid or salt thereof containing the starting alcohol in said solid phase. For example, there may be used a product obtained by substituting the starting alcohol for the water of hydration of the hydrated heteropoly acid or salt thereof or a product obtained by dehydrating the hydrate of heteropoly acid or salt thereof and then allowing the dehydrated product to absorbe an appropriate amount of the starting alcohol. The adduct of the starting alcohol with heteropoly acid or salt thereof may contain not more than 5 moles of water of hydration per mole of heteropoly acid or salt thereof. If the molar ratio of the adduct alcohol to the heteropoly acid or salt thereof in the adduct of the starting alcohol with heteropolyacid or salt thereof is 5 or less, the polymerization of the tertiary olefin tends to be caused, and if the molar ratio is 40 or more, the heteropoly acid or salt thereof is in some case dissolved in the reaction mixture. Therefore, the molar ratio is 5 or more, and preferably 5 to 40.

When the adduct of the starting alcohol with heteropoly acid or salt thereof is directly used without a carrier, the amount of the heteropoly acid or thereof must be 0.1 mole or more per mole of the total of the starting alcohol and the adduct alcohol. The adduct of the starting alcohol with heteropoly acid or salt thereof is preferably supported on a carrier, and a known carrier such as silica, active carbon, alumina or the like is used as the carrier. If active carbon is used as the carrier, the isomerization reaction of an inert olefin such as 1-butene tends to proceed, and hence, silica is particularly preferred as the carrier.

The reaction of the present invention has a sufficient activity at a temperature of about 50° C., and side reactions tend to proceed at an unnecessarily high temperature. The temperature, therefore, is usually not more than 150° C., preferably 0° to 100° C. Such a temperature range is considered also necessary for maintaining the adduct of the starting alcohol with heteropoly acid or salt thereof.

The reaction pressure used in the present invention is a pressure higher than the pressure at which the tertiary olefin is kept in the liquid phase, and the reaction system may be kept under a higher pressure, by applying an inert gas such as nitrogen, helium, argon or the like.

The adduct of the starting alcohol with heteropoly acid or salt thereof must be kept in the solid phase in the present invention; however the adduct is easier to keep in the solid phase at a lower alcohol concentration in the mixture of the alcohol and the tertiary olefin-containing mixed hydrocarbon. Particularly, the adduct is easy to keep in the solid phase when the concentration of the alcohol dissolved in the mixed hydrocarbon is adjusted to 8% by weight or less.

When a large amount of the alcohol is fed, many alcohol-feed inlets may be provided not to allow the alcohol to exist at a high concentration, thereby preventing the dissolution of the adduct. When the alcohol concentration in the starting mixture is 8% by weight or less, one alcohol-feed inlet is sufficient. If the adduct is not dissolved even at an alcohol concentration of 8% by weight or higher (for example, active carbon is used as a carrier), one alcohol-feed inlet is sufficient.

An acidic substance may be added to the adduct of the starting alcohol with heteropoly acid or salt thereof for improving the stability of the adduct. Mineral acids such as phosphoric, sulfuric and hydrochloric acids and the like and organic sulfonic acids such as p-toluenesulfonic acid and the like are used as the acidic substance, and phosphoric acid is preferably used. The acidic substance is added to improve the stability of the catalyst, and hence, a small amount of the acidic substance is sufficient. If the amount is too large, problems of corrosion, side reactions, and the like are caused. Therefore, the amount of the acidic substance used is 2% by weight or less based on the weight of the heteropolyacid or salt thereof.

The process of the present invention may be carried out in any of the continuous, batchwise and semibatchwise manners, and any of the agitated tank, fixed bed and flow method may be used. In this invention, the continuous fixed bed is particularly effective.

BRIEF DESCRIPTION OF THE DRAWING

The FIGURE shows an etherification reactor with multiple feeds.

This invention is further explained in more detail below referring to Examples and the accompanying drawing, which show the reactor used in Example 24 which appears hereinafter. The Examples are merely by way of illustration and not by way of limitation.

EXAMPLE 1

One hundred grams of phosphotungstic acid (manufactured by Nippon Muki Kagaku Kogyo K.K.) was calcined at 300° C. in air for 3 hrs, then cooled and brought into contact with methanol vapor, upon which 20 molecules of the methanol were added to one molecule of the phosphotungstic acid. The resultant adduct was then subjected to vacuum treatment to give 10 moles of the adduct methanol per mole of phosphotungstic acid.

A 300-ml autoclave was charged with the catalyst thus obtained, 2.8 g of methanol, 5.0 g of isobutylene, 50 g of 1-butene and 45 g of n-butane, and the resulting mixture was subjected to reaction at 60° C. at 12 kg/cm$^2$.G for 1 hr, upon which tert-butyl methyl ether was formed in a yield of 97.3% with a selectivity of 100%. The amount of the methanol in the reaction product was 0.01 g or less. None of 2-butene, tert-butanol, dimethyl ether and polymers of isobutylene and 1-butene were detected, and the phosphotungstic acid was not detected from the reaction product.

EXAMPLE 2

Ten grams of phosphotungstic acid was dissolved in 200 g of water, and 40 g of silica gel (Microbeads 5D manufactured by Fuji Davison Co.) was added thereto. After stirring, the moisture was removed from the mixture on a hot water bath. The mixture was then calcined at 300° C. in air for 3 hrs, and 10 g of methanol was absorbed therein to give a catalyst. The reaction was carried out under the same conditions as in Example 1, except that the resultant catalyst was substituted for the catalyst, upon which tert-butyl methyl ether was formed in a yield of 97.7% with a selectivity of 100%. Neither dimethyl ether nor polymers of isobutylene and 1-butene were detected. The reaction product contained 0.01 g or less of methanol, and the reaction system during and after the reaction contained 1 ppm or less of the phosphotungstic acid. Furthermore, no 2-butene was detected.

COMPARATIVE EXAMPLE 1

Reaction was carried out under the same conditions as in Example 1, except that 0.0001 g of phosphotungstic acid calcined at 300° C. in air for 3 hrs was substituted for the catalyst. The yield of the resultant tert-butyl methyl ether was 1.3%. Thus, it is considered that in Examples 1 and 2, the reaction did not proceed with the dissolved heteropoly acid but with the solid phase adduct of the heteropoly acid with the alcohol.

COMPARATIVE EXAMPLE 2

A 300-ml autoclave was charged with 30 g of an ion-exchange resin Amberlist 15, 5 g of isobutylene, 50 g of 1-butene, 45 g of n-butane and 2.8 g of methanol, and the resulting mixture was subjected to reaction at 60° C. at 12 kg/cm$^2$.G to obtain the result shown in Table 1.

TABLE 1

| Reaction time (min) | Yield of tert-butyl methyl ether (%) | Methanol in the reaction system (g) |
|---|---|---|
| 60 | 86 | 0.39 |
| 120 | 86 | 0.39 |

EXAMPLE 3

In 100 g of methanol was dissolved 40 g of phosphotungstic acid, and the resulting solution was adsorbed on active carbon (BAC-MU manufactured by Taiyo Kaken) filtered, washed with methanol, treated at 40 mmHg at 50° C. to remove the excess methanol, whereby 50% of the charged phosphotungstic acid was supported on the active carbon. The reaction was carried out under the same conditions as in Example 1, except that the resultant catalyst was substituted for the catalyst, upon which tert-butyl methyl ether was formed in a yield of 96.3% with a selectivity of 99%. The amount of the methanol in the reaction product was 0.01 g or less, and that of the phosphotungstic acid in the reaction product was 1 ppm or less. No polymers of 1-butene and isobutylene were detected; however 2.5% of the 1-butene was isomerized to 2-butene.

EXAMPLES 4 TO 13

Reaction was carried out under the same conditions as in Example 2, except that silicontungstic acid, 10-tungsto-2-vanadophosphoric acid, 6-tungsto-6-molybdophosphoric acid, phosphomolybdic acid, silicomolybdic acid, germanotungstic acid, borotungstic acid, germanomolybdic acid, tungstofluoric acid (prepared according to the process described in P. Doppelt (et al., Inorg. Chem. Vol. 19, p. 2803), or 18-tungsto-2-phosphoric acid was substituted for the phosphotungstic acid, to obtain the results shown in Table 2. However, in every reaction, the amount of methanol present in the reaction product was 0.01 g or less, and that of the heteropoly acid present was 1 ppm or less.

TABLE 2

| Example No. | Heteropoly acid | tert-Butyl metyl ether | |
|---|---|---|---|
| | | Yield (%) | Selectivity (%) |
| 4 | Silicotungstic acid | 97.4 | 100 |
| 5 | 10-Tungsto-2-vanadophosphoric acid | 97.4 | 100 |
| 6 | 6-Tungsto-6-molybdophosphoric acid | 95.1 | 100 |
| 7 | Phosphomolybdic acid | 93.8 | 100 |
| 8 | Silicomolybdic acid | 94.1 | 100 |
| 9 | Germanotungstic acid | 97.4 | 100 |
| 10 | Borotungstic acid | 97.3 | 100 |
| 11 | Germanomolybdic acid | 93.1 | 100 |
| 12 | Tungstofluoric acid | 93.0 | 100 |
| 13 | 18-Tungsto-2-phosphoric acid | 97.5 | 100 |

EXAMPLE 14

A 300-ml autoclave was charged with 50 g of the same catalyst as in Example 2, 100 g of a mixed hydrocarbon of the composition shown in Table 3 and 2.8 g of methanol, and the resulting mixture was stirred at 60° C. at 12 kg/cm$^2$.G for 1 hr, upon which tert-butyl methyl ether was formed in a yield of 97.8% with a selectivity of 100%. The recovery of 1-butene was 100%. The amount of the methanol in the reaction product was 0.01 g or less, and that of the phosphotungstic acid was 1 ppm or less.

TABLE 3

| | |
|---|---|
| Isobutylene | 5.0 wt. % |
| Isobutane | 9.7 wt. % |
| n-Butane | 29.7 wt. % |
| 1-Butene | 40.0 wt. % |
| 2-Butene | 15.3 wt. % |
| Butadiene | 0.3 wt. % |

EXAMPLE 15

A 300-ml autoclave was charged with 50 g of the same catalyst as in Example 3, 100 g of a mixed hydrocarbon of the composition shown in Table 4 and 24.0 g of methanol, and the mixture was stirred at 60° C. at 12 kg/cm$^2$.G for 30 min, upon which tert-butyl methyl ether was formed in a yield of 98.1% with a selectivity of 100%. The amount of the methanol in the reaction product was 0.05 g, and that of phosphotungstic acid in the reaction system during and after the reaction was 1.0 ppm.

TABLE 4

| | |
|---|---|
| Isobutylene | 42.0 wt. % |
| Isobutane | 2.5 wt. % |
| n-Butane | 18.1 wt. % |
| 1-Butene | 25.0 wt. % |
| 2-Butene | 12.3 wt. % |
| Butadiene | 0.1 wt. % |

EXAMPLES 16 TO 19

A 300-ml autoclave was charged with a catalyst prepared by calcining 10 g of phosphotungstic acid supported on 40 g of silica gel at 300° C. in air for 3 hrs, and absorbing ethanol, n-propanol, isopropanol or n-butanol vapor in the calcined substance, 100 g of a mixed hydrocarbon of the composition shown in Table 3 and 3.3 g of ethanol, 4.5 g of n-propanol, 4.5 g of isopropanol or 5.8 g of n-butanol, and the resulting mixture was stirred at 60° C. at 12 kg/cm$^2$.G for 1 hr to obtain the results shown in Table 5. The amount of the phosphotungstic acid in the reaction system during and after the reaction was 1 ppm or less.

TABLE 5

| Example No. | Alcohol | Resultant ether | |
|---|---|---|---|
| 16 | Ethanol | tert-Butyl ethyl ether | 7.7 g |
| 17 | n-Propanol | tert-Butyl n-propyl ether | 8.5 g |
| 18 | Isopropanol | tert-Butyl isopropyl ether | 8.4 g |
| 19 | n-Butanol | tert-Butyl n-butyl ether | 8.3 g |

EXAMPLE 20

In water were dissolved 10 g of phosphotungstic acid and 0.15 g of phosphoric acid, and 40 g of silica gel (Microbeads 5D manufactured by Fuji Davison) was added to the resulting solution, after which the moisture was removed from the mixture on a hot water bath. The residue was calcined at 300° C. in air for 3 hrs and then cooled, after which 0.03 g of methanol was absorbed in the cooled material to form an adduct of methanol with phosphotungstic acid. Reaction was carried out under the same conditions as in Example 1, except that the resultant catalyst was substituted for the catalyst, upon which tert-butyl methyl ether was formed in a yield of 98.0% with a selectivity of 100%. The amount of the methanol in the reaction product was 0.01 g or less, and the amounts of the phosphotungstic acid in the reaction system during and after the reaction were 1 ppm or less. At this time, none of 2-butene, dimethyl ether and polymers of butenes were detected.

EXAMPLE 21

A 300-ml stainless steel autoclave was charged with 50 g of the same catalyst as in Example 2, 2.8 g of methanol, 6.1 g of 2-methyl-1-butene, 50 g of n-pentene and 43.9 g of pentane, and the mixture was stirred at 60° C. and 8 kg/cm$^2$.G for 1 hr, upon which 2-methoxy-2-methyl-butane was formed in a yield of 91.4% with a selectivity of 99%. The amount of the methanol in the reaction product was 0.01 g or less, and no phosphotungstic acid was detected in the reaction system during and after the reaction.

EXAMPLE 22

A catalyst was prepared by the same method as in Example 2, except that alumina (Neobead, manufactured by Mizusawa Kagaku), and reaction was carried out under the same conditions as in Example 2, except that the resultant catalyst was substituted for the catalyst and the reaction time was changed from 1 hr to 2 hrs, upon which tert-butyl methyl ether was formed in a yield of 95.1% with a selectivity of 100%. The amount of the methanol in the reaction product was 0.01 g or less, and the amounts of the phosphotungstic acid in the reaction system during and after the reaction were 1 ppm or less.

EXAMPLE 23

Ten grams of phosphotungstic acid was supported on 40 g of silica gel (Microbeads 5D, manufactured by Fuji Davison), and calcined at 300° C. in air for 3 hrs. A stainless steel fixed bed reactor having an inside diameter of 1 cm was packed with the calcined product, and the interior of the reactor was kept at 60° C. and 12 kg/cm$^2$.G, after which a mixture of 100 g of a mixed hydrocarbon having the composition shown in Table 3 with 3.8 g of methanol was fed thereto at a rate of 100 g/hr for 1 hr. A mixture of 100 g of mixed hydrocarbon having the composition shown in Table 3 with 2.7 g of methanol was thereafter fed to the reactor at a rate of 100 g/hr, upon which tert-butyl methyl ether was obtained as an effluent at a rate of 7.5 g/hr. The amount of the phosphotungstic acid in the effluent was 1 ppm or less, and the rate of effluent methanol was 0.007 g/hr.

EXAMPLE 24

A stainless steel fixed bed reactor having an inside diameter of 2 cm was packed with 500 g of the same catalyst as in Example 2. A mixed hydrocarbon having the composition shown in Table 4 was fed to the reactor at a rate of 1.0 kg/hr, while methanol was fed from 10 inlets as shown in the accompanying drawing each at a rate of 22.9 g/hr. The interior of the reactor was kept at 60° C. and at 12 kg/cm².G. tert-Butyl methyl ether flowed out of the reactor at a rate of 627 g/hr, and methanol flowed out thereof at a rate of 0.1 g/hr. The amount of the phosphotungstic acid in the effluent was 0.9 ppm.

EXAMPLE 25

Reaction was carried out under the same conditions as in Example 24, except that methanol was fed from 10 inlets each at a rate of 25.3 g/hr, upon which tert-butyl methyl ether was formed at a rate of 655 g/hr, and methanol flowed out at a rate of 14.8 g/hr. The amount of the phosphotungstic acid in the effluent was 1.0 ppm.

EXAMPLE 26

Reaction was carried out under the same conditions as in Example 23, except that a catalyst prepared by using phosphomolybdic acid instead of the phosphotungstic acid was substituted for the catalyst, upon which tert-butyl methyl ether flowed out at a rate of 7.5 g/hr. The amount of the methanol in the effluent was 0.007 g/hr, and the amount of the phosphomolybdic acid in the effluent was 1 ppm or less.

EXAMPLES 27-49

Reaction was carried out under the same conditions as in Example 2, except that a catalyst wherein a heteropoly acid salt as shown in Table 6 was supported, instead of the phosphotungstic acid, on silica prepared under the same conditions as in Example 2 was substituted for the catalyst and the reaction time was 3 hrs. The results obtained are shown in Table 6.

In all the reactions, the amount of methanol in the reaction product was 0.01 g or less, and that of heteropoly acid salt was 1 ppm or less.

TABLE 6

| Example No. | Heteropoly acid salt | tert-Butyl methyl ether Yield (%) | Selectivity (%) |
|---|---|---|---|
| 27 | Lithium silicotungstate | 97.5 | 100 |
| 28 | Magnesium 10-tungsto-2-vanadophosphate | 97.3 | 100 |
| 29 | Calcium 6-tungsto-6-molybdophosphate | 96.4 | 100 |
| 30 | Barium phosphomolybdate | 95.1 | 100 |
| 31 | Ditetraethylammonium dihydrogen silicomolybdate | 97.8 | 100 |
| 32 | Zirconium germanotungstate | 97.1 | 100 |
| 33 | Chromium phosphotungstate | 97.2 | 100 |
| 34 | Manganese phosphotungstate | 97.1 | 100 |
| 35 | Iron phosphotungstate | 97.5 | 100 |
| 36 | Cobalt phosphotungstate | 97.0 | 100 |
| 37 | Nickel phosphotungstate | 97.5 | 100 |
| 38 | Copper phosphotungstate | 97.4 | 100 |
| 39 | Silver silicotungstate | 96.9 | 99 |
| 40 | Zinc silicotungstate | 97.3 | 100 |
| 41 | Cadmium silicotungstate | 95.2 | 100 |
| 42 | Mercury silicotungstate | 94.9 | 100 |
| 43 | Aluminum silicotungstate | 97.8 | 100 |
| 44 | Lead silicotungstate | 97.2 | 100 |
| 45 | Bismuth silicotungstate | 96.3 | 100 |
| 46 | Dipotassium dihydrogen-silicotungstate | 97.9 | 100 |
| 47 | Tricesium monohydrogen-silicotungstate | 97.1 | 100 |
| 48 | Ammonium dihydrogenphosphotungstate | 97.7 | 100 |
| 49 | Sodium phosphotungstate | 96.4 | 99 |

What is claimed is:

1. A process for preparing an ether having a tertiary alkyl group by reacting a primary or secondary alcohol with a tertiary olefin represented by the formula, $$R^1HC=CR^2R^3$$

wherein $R^1$ is hydrogen or an alkyl group, and $R^2$ and $R^3$ are alkyl groups, contained in a tertiary olefin-containing mixed hydrocarbon, characterized in that said reaction is carried out at a pressure higher than the pressure at which the tertiary olefin-containing mixed hydrocarbon is kept in the liquid phase, in the presence of an adduct of the starting alcohol with a heteropoly acid or salt thereof containing at least one element selected from the group consisting of P, Si, B, Ge, As, Se, Ti, Zr, Mn, F, U, Ce and Th as a central element, at least Mo and/or W as a coordinating element and containing a cation comprising at least one of H, Li, Na, K, Rb, Cs, $NR^4R^5R^6R^7$ in which $R^4$, $R^5$, $R^6$ and $R^7$ are hydrogen atoms or alkyl groups, Mg, Ca, Ba, Zr, Cr, Mn, Fe, Co, Ni, Cu, Ag, Zn, Cd, Hg, Al, Pb and Bi, the ratio of the number of the coordinating elements to the number of the central elements being 2.5 to 12, the adduct being in a substantially solid-phase state.

2. A process according to claim 1, wherein the molar ratio of the primary or secondary alcohol to the tertiary olefin is 1.2 or less.

3. A process according to claim 1 or 2, wherein the concentration of the primary or secondary alcohol dissolved in the mixed hydrocarbon is 8% by weight or less.

4. A process according to any one of claims 1 to 3, wherein the adduct of the starting alcohol with the heteropoly acid or salt thereof is supported on silica.

5. A process according to any one of claims 1 to 3, wherein the adduct of the starting alcohol with heteropoly acid or salt thereof is supported on active carbon.

6. A process according to claim 1, wherein the heteropoly acid contains at least one element selected from the group consisting of P, Si, B and Ge as the central element.

7. A process according to claim 1 or 6, wherein the heteropoly acid contains at least one of the cations of H, Na, Zn, Al and Pb.

8. A process according to claim 1 or 6, wherein the heteropoly acid contains $H^+$.

9. A process according to claim 1, wherein a part of the coordinating element may be replaced by at least one element selected from the group consisting of V, Mn, Co, Ni, Cu, Zn, and Fe.

* * * * *